United States Patent [19]

Radtke et al.

[11] Patent Number: 5,013,748

[45] Date of Patent: May 7, 1991

[54] EMULSIFIABLE BIOCIDAL CONCENTRATES FOR WOOD PRESERVATION

[75] Inventors: Damien Radtke, Saint-Juery; Edmond Wozniak, Labruguiere, both of France

[73] Assignee: Xylochimie, Neuilly Sur Seine, France

[21] Appl. No.: 307,740

[22] Filed: Feb. 8, 1989

[30] Foreign Application Priority Data

Feb. 8, 1988 [FR] France ............................... 88 01660

[51] Int. Cl.⁵ ..................... A01N 43/64; A01N 43/52
[52] U.S. Cl. ..................................... 514/383; 514/394
[58] Field of Search ................................ 514/383, 394

[56] References Cited

FOREIGN PATENT DOCUMENTS 984660 8/1986 Belgium .
148526 7/1985 European Pat. Off. .

OTHER PUBLICATIONS

Richardson, "Wood Preservation" The Construction Press, pp. 167–168, 1979.

*Primary Examiner*—John W. Rollins
*Attorney, Agent, or Firm*—Burns, Doane, Swecker & Mathis

[57] ABSTRACT

Liquid biocidal concentrates which can be diluted into aqueous microemulsions useful for wood preservation, contain (A) at least one triazole fungicide, at least one quaternary ammonium fungicide, and at least one benzimidazole fungicide, and (B) a combination liquid solvent medium therefor, including an ether of an alkanol and of a diol, as well as a carboxylic acid, and, optionally, (C) an additive comprised of oil(s) and/or fixative(s).

15 Claims, No Drawings

EMULSIFIABLE BIOCIDAL CONCENTRATES FOR WOOD PRESERVATION

BACKGROUND OF THE INVENTION

1. Field of the Invention

The present invention relates to liquid organic concentrates permitting the preparation of biocidal aqueous microemulsions useful for the protection of freshly felled and sawn timber, and to the aqueous microemulsions produced by adding water to such concentrates. This invention also relates to the use of such microemulsions for ensuring the protection of freshly felled and sawn timber, at least against the fungal deep blue stain of timber and the development of surface moulds thereon.

2. Description of the Prior Art

Protecting or preserving timber by impregnating it, e.g., by soaking or spraying it with fungicidal and/or insecticidal substances has long been known to this art. The active substance, preferably one that is water-insoluble, is dissolved, for example, in a suitable liquid medium to form a concentrate. The dissolving medium usually comprises one or more organic solvents for the active substance, mixed, if desired, with one or more oils and/or with one or more fixing agents. At the point in time of its use for impregnating the timber to be treated, the liquid concentrate is diluted with water and stirred so as to form an emulsion, and it is this emulsion which is definitively applied onto the surface to be treated.

Fresh timbers abound in sap which is rich in easily assimilable substances which create a nutrient medium for various biological organisms including, in particular, the agents responsible for fungal blue stain and agents responsible for moulds. The agents responsible for blue stain consist particularly of cellulolytic imperfect fungi which can develop quickly and enter deeply into the cells of the timber cores and whose mycelium is dark in color. While the damage produced has no detrimental effect on the physical and mechanical properties of the timber, on the other hand, the aesthetic qualities of the sapwood are greatly altered. Exemplary of such fungi are *Aureobasidium pullulans, Sclerohoma piytohila* and *Hormonema dematioides*. The agents responsible for moulds in this case also consist particularly of imperfect fungi, generally cellulolytic, which develop on the surface of the timber in moist conditions such as those encountered in countries with a temperate climate, producing fruiting organs of various shapes and colors, which are detrimental to the aesthetic appearance of the timber. Exemplary of such fungi are *Aspergillus spp, Trichoderma spp, Penicillium spp* and *Cladosoorium spp*.

Good temporary fungicidal protection of fresh timber requires the availability of a treatment formulation:

(i) containing oen or more fungicidal active agent(s) capable of combating the attack by fungi responsible for the deep blue stain and the surface moulds, and (ii) exhibiting a twofold behavior; a first behavior according to which the treatment product must be able to effect penetration of the timber by th fungicidal substance(s) provided for combating the attack by the organisms responsible for the blue stain; and a second, simultaneous behavior, according to which the treatment product must be capable of creating, at the same time, an antimould surface barrier while allowing the fungicidal substance(s) intended for combating the attack of the organisms responsible for moulds to be maintained at the surface of the timber.

Belgian Patent BE-A-904,660 describes a fungicidal aqueous emulsion obtained by diluting, with water, a concentrate based on two fungicidal substances and an appropriate solvent for these fungicides. The fungicidal substances employed are: on the one hand, a derivative of imidazole or of 1,2,4-triazole and, on the other hand, a quaternary ammonium salt derived from an organic or inorganic acid. An emulsion of this type, prepared from a concentrate containing, for example, 1H-1-[2-(2,4-dichlorophenyl)-1,3-dioxolanyl-2-methyl]-1,2,4-triazole (known as azaconazole) and benzalkonium chloride as fungicidal substance, has been found to be advantageous because it enables the fungicidal substances to penetrate into the timber quite deeply (probably by virtue of the surfactant effect which the quaternary ammonium salt can also develop); on the other hand, it is found that this emulsion does not provide an effectively antimould barrier at the surface of the timber.

SUMMARY OF THE INVENTION

Accordingly, a major object of the present invention is the provision of an improved formulation for treating fresh timber, which is effective both in combating deep blue stain, as well as surface moulds.

Another object of the present invention is the provision of an improved formulation for treating timber, permitting the preparation of aqueous microemulsions which are known to have excellent application properties for the treatment of timber.

Yet another object of the present invention is the provision of an improved formulation for treating timber, which is capable, if need be, of additionally comprising one or more insecticidal substances and a surface-active agent which is appropriate for this active substance, without interfering with attaining those objectives outlined above.

Briefly, the present invention features water-emulsifiable, liquid concentrates which comprise:

(A) an effective amount of an active agent comprising:

(a1) at least one fungicidal compound having the formula:

in which Q is N or CH; and R is one of the radicals:

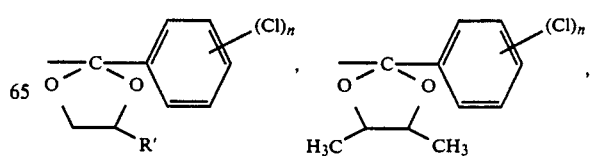

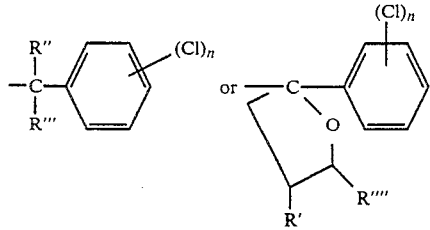

in which R' is a hydrogen atom or a linear or branched chain alkyl radical containing from 1 to 3 carbon atoms, R" is a hydrogen atom or a hydroxyl or cyano group, R''' is a linear or branched chain alkyl radical containing from 1 to 6 carbon atoms (optionally substituted by a cycloalkyl group or a phenyl group), an alkenyloxy radical containing from 3 to 4 carbon atoms or a phenyl radical (optionally substituted by one or more halogen atom(s)), R'''' is a hydrogen atom or a linear or branched chain alkyl radical containing from 1 to 3 carbon atoms (optionally substituted by one or more halogen atom(s)), and D is an integer equal to 1 or 2; and (a2) at least one fungicidal compound having the formula:

(cationic moiety)   (anionic moiety)

in which the cationic moiety of the salt has a total number of carbon atoms equal to or less than 50, and $R_1$, $R_2$, $R_3$ and $R_4$ are identical or different organic radicals, the free valency of which is borne by a carbon atom, with the proviso that one of the radicals $R_1$, $R_2$, $R_3$ or $R_4$ may be a hydrogen atom, or another ammonium group if desired, and with the further provisos that, if desired, two of such radicals may together form a single divalent radical, three of such radicals, if desired, may together form a single trivalent radical, and two pairs of such radicals, if desired, may together form two single divalent radicals; and the anionic moiety X is derived from an inorganic or organic acid; and (B) a liquid carrier for the active agent comprising:
(b1) the medium for dissolving the active agent;
(b2) if desired, at least one oil; and
(b3) if desired, at least one fixing agent; the said concentrates being characterized in that the active agent (A) additionally comprises (a3) at least one fungicidal compound selected from among:
(i) a benzimidazole compound having the formula:

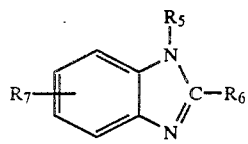

in which $R_5$ is a hydrogen atom or a —CO—$NR_8R_9$ group wherein $R_8$ is a hydrogen atom or a linear or branched chain alkyl radical containing from 1 to 4 carbon atoms and $R_9$ is a linear or branched chain alkyl radical containing from 1 to 6 carbon atoms, a phenyl radical or a benzyl radical, or a substituted such radical substituted by a lower alkyl group or a lower alkoxy group; $R_6$ is a hydrogen atom, an amino group —$NH_2$, and —NH—CO—$OR_8$ group or an —NH—CO—NH—$OR_8$ group wherein $R_8$ is an alkyl radical as defined above, or a 4-thiazolyl group, with the proviso that $R_6$ may form a single ring with $R_5$ and the atoms to which these radicals are bonded; and $R_7$ is a hydrogen atom or a hydroxyl group; and (ii) a mixture of one or more of the compounds of formula (III) with one or more derivatives of isothiazolinone; and the medium (b1) for dissolving the active agent comprises at least two necessary solvents (b1.1) and (b1.2), with (b1.1) comprising an ether of a lower alkanol containing from 1 to 4 carbon atoms and of a saturated aliphatic diol containing from 2 to 10 carbon atoms, and (b1.2) comprising a saturated aliphatic monocarboxylic acid containing from 1 to 6 carbon atoms.

DETAILED DESCRIPTION OF THE PREFERRED EMBODIMENTS OF THE INVENTION

More particularly according to the present invention, as a general rule, the proportions of the constituents of a given fungicidal liquid concentrate are selected between the following limits (expressing the percentage by weight of each of the constituents in the concentrate):

(a) from 3% to 8% of fungicidal compound(s) (a1);
(b) from 15% to 40% of fungicidal compound(s) (a2);
(c) from 0.1% to 2% of fungicidal compound(s) (a3);
(d) an amount of solvents (b1) equal to or greater than 50%; and
(e) from 0% to 20% of oil(s) (b2) and/or of fixing agent(s) (b3).

As regards the fungicidal compound(s) (a1), exemplary compounds are those corresponding to the formula (I), in which Q=N. Especially representative are those compounds having the following formulae:

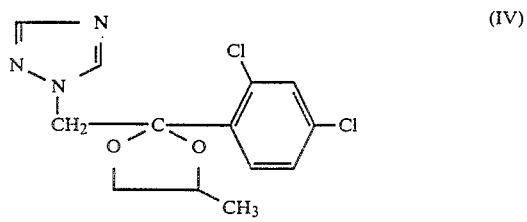

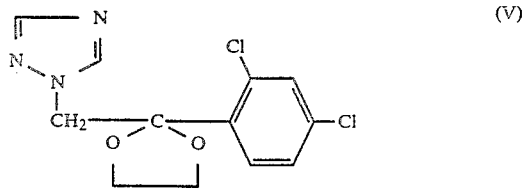

(this compound is well known to the art as azaconazole)

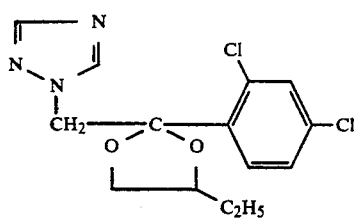
(VI)

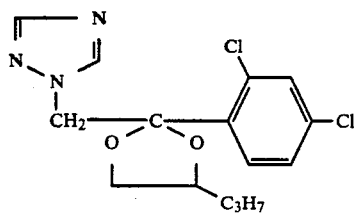
(VII)

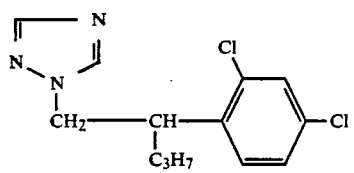
(VIII)

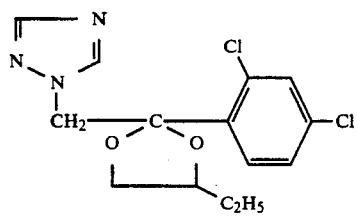
(IX)

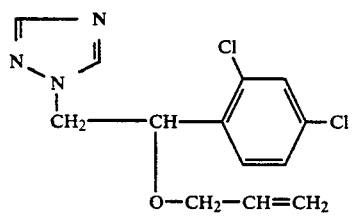
(X)

and

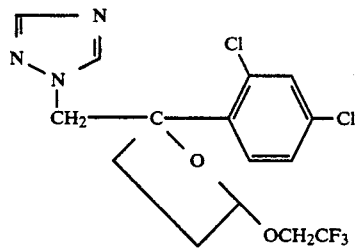
(XI)

The compounds of formulae (I) and (IV) to (XI) may be prepared according to the procedures given, for example, in U.S. Pat. Nos. 3,575,999, 3,717,655, 3,636,002, 3,927,017, 4,156,008 and 4,079,062 and in EP-A-0,230,844.

As regards the fungicidal compound(s) (a2), one or more salts of formula (II) are used, in which the anionic moiety originates from an inorganic or organic acid. By "inorganic or organic acid" is intended a mono- or polyacid in which at least one of the acidic groups has a constant of ionization in water, $pK_a$, which is lower than or equal to 7. As acids of this type, representative are, among the inorganic acids, hydrochloric, sulfuric, orthophosphoric and pyrophosphoric acids; among the organic acids are organosulfonic acids, particularly para-toluenesulfonic, methanesulfonic, benzenesulfonic, naphthalenesulfonic, organophosphonic acids, particularly monoalkyl- or monoarylphosphonic acids such as methylphosphonic or benzenephosphonic, mono- or polycarboxylic acids such as acetic or propionic acids, or their dihalo- and trihalo-(particularly chloro and fluoro) derivatives.

Quaternary ammonium salts are preferably employed as salts of formula (II). More specifically, the cationic moiety of these salts exhibits the following features: the various radicals $R_1$, $R_2$, $R_3$ and $R_4$ may be:

(i) aliphatic (linear or branched), cycloaliphatic or aromatic (of the aryl or arylaliphatic type) saturated or unsaturated hydrocarbon radicals;

(ii) radicals comprising a number of oxyalkylene recurring units, for example radicals of the formula:

$$-R_{10}-(O-R_{10})_t-OH$$

wherein t ranges from 1 to 10 and $R_{10}$ is a radical $-CH_2-$, $-CH_2-CH_2-$ or $-CH_2-CH(CH_3)-$;

with the provisos that one of the radicals $R_1$, $R_2$, $R_3$ or $R_4$ may be a quaternary ammonium radical of the formula:

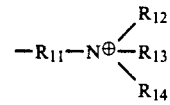

wherein $R_{12}$, $R_{13}$ and $R_{14}$ are hydrocarbon radicals or radicals containing oxyalkylene groups such as defined above in the case of $R_1$, $R_2$, $R_3$ and $R_4$, and $R_{11}$ is a divalent aliphatic or aromatic (particularly of the arylaliphatic type) hydrocarbon radical in which the carbon chain(s) may be interrupted by oxygen atoms, the free valencies of the radical $R_{11}$ being borne by aliphatic carbon atoms; and one or more pairs of the radicals $R_1$, $R_2$, $R_3$ and $R_4$ may together form a single divalent alkylene or oxyalkylene radicals.

As ammonium salts of formula (II) which are more particularly preferred, especially representative are trimethylalkylammonium salts such as, for example, trimethyldecylammonium, trimethyldodecylammonium, trimethylhexadecylammonium, trimethyloctadecylammonium or trimethylalkylammonium chloride or propionate in which the alkyl chain is a mixture of alkyl radicals from $C_8H_{17}$ to $C_{18}H_{37}$, dimethyldialkylammonium salts such as, for example, dimethyldidecylammonium, dimethyldidodecylammonium, dimethyldihexadecylammonium, dimethyldioctadecylammonium and diemthyldialkylammonium chloride or propionate in which the alkyl chains are a mixture of alkyl radicals from $C_8H_{17}$ to $C_{18}$, dimethylalkylbenzylammonium salts such as, for example, dimethyldecylbenzylammonium, dimethyldodecylbenzyammonium, dimethylhexadecylbenzylammonium, dimethyloctadecylbenzylammonium or dimethylalkylbenzylammonium chloride or propionate, in which the alkyl chain is a mixture of alkyl radicals from $C_8H_{17}$ to $C_{18}H_{37}$ (this salt is well known to the art as benzalkonium chloride or propionate).

As regards the fungicidal compound (s) (a30, exemplary such benzimidazole compound are those corresponding to the following formulae:

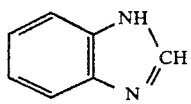

(XII)
benzimidazole

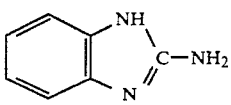

(XIII)
2-aminobenzimidazole

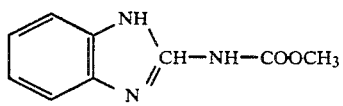

(XIV)
2-(methoxycarbonyl-amino)benzimidazole

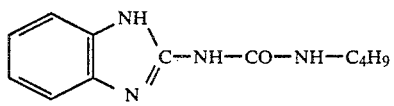

(XV)
2-(3-butylureido)-benzimidazole

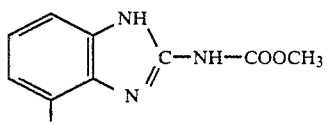

(XVI)
2-(methoxycarbonyl-amino)-4-hydroxy-benzimidazole

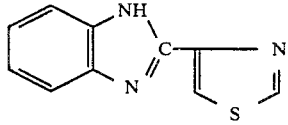

(XVII)
2-(4-thiazolyl)-benzimidazole

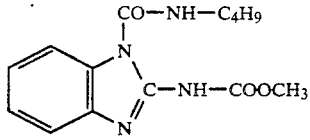

(XVIII)
1-(butylaminocarbonyl)-2-(methoxycarbonylamino)-benzimidazole (known to the art as benomyl).

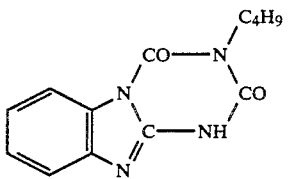

(XIX)

As regards the isothiazolinone derivatives which may comprise the fungides (a3) of this type, representative are, for example 5-chloro-2-methyl-4-isothiazolin-3-one and/or 2-methyl-4-isothiazoline-3-one. The compounds of formulae (III) and (XII) to (XIX) are knwon compounds of the prior art, some of which are available commercially, e.g., benomyl.

A fungicidal active substance which is particularly advantageous according to the invention is the combination (a1)+(a2)+(a3), in which (a1) is azaconazole, (a2) is a dimethylalkylbenzylammonium salt and (a3) is 2-(methoxycarbonylamino)benzimidazole and/or benomyl.

With respect to the liquid carrier (B) according to the invention and, more particularly, with respect to the medium (b1) for dissolving the active substance, this comprises at least two obligatory solvents (b1.1) and (b1.2), with (b1.1) comprising an ether of an alkanol and of a diol, and (b1.2) comprising a monocarboxylic acid. Another medium for dissolving which may be employed is that containing a mixture of three solvents: (b1.1) +(b1.2) +(b1.3), with (b1.3) comprising a saturated aliphatic diol containing from 2 to 10 carbon atoms. Another dissolving medium which can be employed is that containing a mixture of three solvents: (b1.1)+(b1.2)+water. Yet another dissolving medium which can be employed is that containing a mixture of four solvents: (b1.1)+(b1.2)+(b1.3) water.

Among the solvents of type (b1.1) which may be employed, exemplary are, in particular: diethylene glycol monomethyl ether, diethylene glycol dimethyl ether, diethylene glycol monoethyl ether, diethylene glycol diethyl ether, propylene glycol monomethyl ether and dipropylene glycol monomethyl ether.

Among the solvents of type (b1.2) which may be employed, exemplary are, in particular: formic acid, acetic acid and propionic acid.

Among the solvents of type (b1.3) which may be employed, exemplary are, in particular: ethylene glycol, diethylene glycol, propylene glycols, butylene glycols and hexylene glycol.

The relative proportions of each solvent in their mixtures are not critical and may vary over wide limits.

The solvent mixtures which are suitable according to the present invention advantageously comprise the binary mixtures (b1.1)+(b1.2) defined above, containing 60 to 95% by weight of solvent (b1.1) and 40 to 5% by weight of solvent (b1.2). When ternary or quaternary solvent mixtures are employed, care is preferably taken that:

(i) on the one hand, the pair of necessary solvents (b1.1)+(b1.2) has the composition indicated above, and (ii) on the other hand, the weight proportion of the said pair of solvents relative to the total weight of the mixtures in question, that is to say: (b1.1)+(b1.2)+(b1.3), (b1.1)+(b1.2)+H20, and (b1.1)+(b1.2) +(b1.3) +H$_2$O, generally represents at least 50%.

As oil(s) (b2) which may be employed in the liquid carrier (B), exemplary are, in particular: a vegetable oil such as, for example, linseed oil, soya oil, pine oil, tall oil and a mixture of terpineols, and an inorganic oil such as, for example, spindle oil, which is a petroleum distillation fraction intermediate between lamp oils and paraffins.

As mentioned above, the liquid carrier (B) may also comprise one or more adhesive agents (b3) capable of fixing the treatment agent on the timber. Representative are, for example: starch, carboxymethyl cellulose, colophony or colophony esters, gum arabic, polyvinyl alcohol, humic acid, glycerophthalic resins, and so-called hydrocarbon resins which are low polymers of aliphatic and/or aromatic unsaturated hydrocarbons originating from the cracking of indene-rich petroleum fractions.

The active agent (A) of the concentrates according to the present invention may, in addition, contain (a4) at least one water-insoluble insecticidal compound. The insecticides which may be employed are products which are known to protect timber against the attack by xylophagous insects such as, in particular, termites, capricorn beetles, deathwatch beetles and powder post beetles. Exemplary of such compounds which are suitable according to the present invention, representative are: organohalogen compounds such as, for example, DDT (dichlorodiphenyltrichloroethane), methoxychlor (dimethoxydiphenyltrichloroethane), lindane ($\gamma$-isomer of hexachlorocycohexane), chlordane (octachlorohexahydromethanoindene), aldrin (endo hexachlorohexahydrodimethanonaphthalene), toxaphene, organophosphorus compounds such as, for example, diethion (0,0,0',0'-tetraethyl-S,S'methylenedithiophosphate), parathion (0,0-diethyl-paranitrophenyl thiophosphate), phosalone (0,0-diethyl-3-dithiophosphorylmethyl-6-chlorobenzoxazolone), insecticidal carbamates such as, for example, sevin (naphthyl N-methylcarbamate) or carbofuran (dimethyldihydrobenzofuryl N-methylcarbamate), synthetic pyrethrinoids such as, for example, decamethrin ($\alpha$-cxyanophenoxybenzyl dibromovinyl-dimethylcyclopropanecarboxylate), cypermethrin (phenoxybenzyl cis-trans-dimethyldichlorovinylcyclopropanecarboxylate) and fenvalerate ($\alpha$-cyanophenoxybenzyl chlorophenylmethylbutylbutyrate).

In the case of use of a single active agent based on fungicidal compounds and on insecticidal compound(s), the liquid carrier (B) for the concentrates according to th invention will additionally contain, beside the obligatory (b1) and optional ingredients (b2) and (b3) defined above, a surface-active agent (b4) comprising a nonionic surfactant preferably belonging to the group of polyoxyalkylated fatty alcohols, polyoxyalkylated fatty acid-alcohols, polyoxalkylated phenols, polyoxyalkylated phenylphenols and polyoxyalkylated alkylphenols obtained by condensing 5 to 80 moles of alkylene oxide, particularly ethylene oxide, with a saturated or unsaturated fatty alcohol or fatty acid-alcohol containing from 8 to 22 carbon atoms, phenol, a phenylphenol or an alkylphenol in which the alkyl residue contains at least 4 carbon atoms.

These nonionic surface-active agents are known to the art and have been widely described in the literature. For the choice of the surface-active agent (b4), reference may be made, for example, to the *Encyclopedia of Chemical Technology*, Kirk-Othmer, volume 22, pages 332–432, 3rd edition (1983). As examples of nonionic surface-active agents there may be mentioned the product available commercially under the registered mark Soprophor B, which is obtained by the addition of ethylene oxide to castor oil.

In the case of the use of an active agent based on fungicidal compounds and on insecticidal compound(s), it may be necessary, in certain cases, for the dissolving medium (bl) to contain, in addition, beside the mixtures of solvents (b1.1)+(b1.2), (b1.1)+(b1.2)+$H_2O$, (b1.1)+(b1.2)+(b1.3) or (b1.1)+(b1.2)+(b1.3)+$H_2O$, an additional solvent (b1.4) which is perfectly adapted to the insecticidal compound(s) employed. As solvents of type (b1.4) which may then be employed, exemplary are, in particular: liquid aromatic hydrocarbons such as, for example, chlorobenzene, dichlorobenzene, toluene, xylenes or mixtures of aromatic hydrocarbons originating directly from petroleum distillation, such as lamp oils, which are distillation fractions included in a temperature range from 150° to 300° C., monoalcohols such as, for example, cyclohexanol, aliphatic ketones such as, for example, ethyl amyl ketone or diisobutyl ketone, esters such as, for example, butyl or nonyl phthalates or dimethyl or diethyl succinates, adipates, oxalates or malonates, and amides such as, for example, dimethylformamide or dimethylacetamide. It should further be noted that it is possible, and sometimes even advantageous, to include the insecticidal compound(s) in the form of a solution in a solvent of (b1.1), (b1.3) or (b1.4) type, depending on the nature of the insecticidal compound(s) employed. When an additional solvent (b1.4) is used, care is preferably taken, as indicated above, that:

(i) on the one hand, the pair of obligatory solvents (b1.1)+(b1.2) has the composition defined above, according to which the pair contains 60 to 95% by weight of solvent (b1.1) and 40 to 5% by weight of solvent (b1.2), and (ii) on the other hand, the proportion of the pair of solvents (b1.1) +(b1.2) represents at least 50% of the total weight of the possible mixtures, that is to say: (b1.1) +(b1.2)+(b1.4), (b1.1)+(b1.2)+(b1.3)+(b1.4), (b1.1) +(b1.2)+$H_2O$+(b1.4), and (b1.1)+(b1.2)+(b1.3)+H20 +(b1.4).

As a general rule, the proportions of the constituents of a fungicidal and insecticidal liquid concentrate in accordance with the present invention are selected within the following limits (expressing the percentage by weight of each of the constituents in the concentrate):

(a) from 3% to 8% of fungicidal compound(s) (a1);
(b) from 15% to 40% of fungicidal compound(s) (a2);
(c) from 0.1% to 2% of fungicidal compound(s) (a3);
(d) from 1% to 10% of insecticidal compound(s) (a4);
(e) an amount of solvents (bl) which is equal to or greater than 20%;
(f) from 0% to 20% of oil(s) (b2) and/or fixing agent(s) (b3); and
(g) from 5% to 20% of surface-active agent (b4).

Insecticidal compounds (a4) which are advantageous include lindane, phosalone, sevin, cypermethrin, fenvalerate, or mixtures thereof.

The fungicidal liquid concentrates according to the present invention may be formulated in the following manner, and this is a preferred method:

(1) the fungicidal compound(s) (a2) is (are) dissolved in the liquid carrier (B), comprising the dissolving medium (bl) +optionally one (or more) oil(s) (b2) + optionally one (or more) fixing agent(s) (b3), by heating the mixture to a temperature of from 30° C. to 60 C., and then (2) the fungicidal compound(s) (a1) is (are) added and the mixture, maintained at the above-mentioned temperature, is stirred mechanically until the compound(s) (a1) has (have) dissolved completely, and finally (3) the fungicidal compound(s) (a3) is (are) added, while the temperature is still maintained at the above-mentioned value.

The fungicidal and insecticidal liquid concentrates according to the present invention may also be formulated in the following manner, and this too is a preferred method:

(1') the sequence of steps (1), (2) and (3) defined above is carried out, and then (2') the mixture is allowed to cool to 20° C., and (3') the surface-active agent (b4), on the other hand, which is (are), in a very preferred manner, in the form of a solution in a solvent of type (b1.1), (b1.3) or (b1.4), are added in succession and with mechanical stirring.

Pigments and/or colorants may very well be added into the liquid concentrates in accordance with the present invention, in order to dye the wood to be treated.

The concentrates obtained are in the form of a transparent liquid which is perfectly stable in storage at temperatures of from $-10°$ C. to $+30°$ C.

The microemulsions obtained from the concentrates according to the invention and intended for protecting fresh timber against blue stain, particularly deep blue stain, and the development of moulds on the surface and, if desired, against insects, are prepared simply by adding the concentrate containing the selected biocides into the desired mass of water, under stirring. They are characterized by a translucent to transparent appearance.

An emulsion of this type is commonly called a microemulsion or, more rarely, a micellar solution, in contrast to a macroemulsion, which is milky in appearance. The microemulsions according to the invention are also characterized by good stability over time; their viscosity and surface tension are also very low. These characteristics: microemulsion, good stability, low viscosity, relatively low surface tension, endow the emulsions according to the invention with excellent properties for application in the treatment of timber.

The microemulsions contain the concentrate according to the invention and water in a mutual weight ratio which may vary from 2/98 to 10/90, preferably from 2/98 to 5/95. Such microemulsions are obtained by adding 1 part by weight of the concentrate to 9 to 49 parts by weight of water, and preferably to 19 to 49 parts by weight of water.

The aqueous microemulsions according to the invention may be applied to rresh timber in order to protect it by following methods which are in themselves known to the art, preferably methods using coating, drenching, spraying or by using impregnation methods, for example by soaking, by pressurizing and/or by subjecting to vacuum.

In order to further illustrate the present invention and the advantages thereof, the following specific example is given, it being understood that same is intended only as illustrative and in nowise limitative.

EXAMPLE

This example describes an emulsifiable fungicidal concentrate in accordance with the invention and a test on timber carried out using an aqueous microemulsion prepared from this concentrate. It will be shown that the protection of timber against deep blue stain and the development of moulds on the wood surface is unquestionably better ensured with the treatment formulations according to the invention than with the treatment formulations in accordance with the prior art.

(1) Emulsifiable concentrate

It had the following composition by weight:

(i) 5.3% of azaconazole, a fungicidal compound of type (a1) corresponding to formula (V);

(ii) 37.3% of benzalkonium chloride, a fungicidal compound of type (a2);

(iii) 0.26% of benomyl, a fungicidal compound of type (a3), corresponding to formula (XVIII);

(iv) 53.3% of propylene glycol monomethyl ether, a solvent of type (b1.1); and (v) 3.84% of acetic acid, a solvent of type (b1.2).

To prepare this concentrate, the above-mentioned solvents (b1.1) and (b1.2) and benzalkonium chloride were charged into a dissolver equipped with a stirring system, a heating system and the conventional attachments related to equipment of this type, and the entire mass was heated to 40° C. Azaconazole was then added and this mixture was stirred while being maintained at 40° C. such as to ensure complete dissolution of the solid biocides introduced (this step required approximately 20 minutes). Lastly, benomyl was added while the temperature was maintained at 40° C.; its dissolution was quick, requiring approximately 5 minutes.

The emulsifiable concentrate obtained had a relative density of 0.9384 at 20° C. It was very stable: it did not crystallize at $-5°$ °C. and, at $+40°$ C., after several days at this temperature, no deposit was observed at the bottom of the receptacle containing it.

(2) Microemulsion

This was prepared by mixing, under stirring, 1 part by weight of concentrate with 29 parts by weight of water (a dilution of 3.33% by weight). A microemulsion of the oil-in-water type was easily obtained, with the aqueous continuous phase being transparent in appearance.

The stability of this microemulsion was very good. A stability test was carried out in accordance with NF standard X 41-580. This test consisted, in particular, in measuring the degree of phase separation under specified conditions, by determining the quantity of cream or deposit which formed after the emulsion had been at rest. The absence of phase separation was observed after a rest period of 1 hour, 30 minutes, at $+20°$ C.; after a rest period of 24 hours, the absence of phase separation was still observed. Furthermore, after 5 freeze/thaw cycles (from $-10°$ C. to $+20°$ C.) had been carried out, it was observed that the microemulsion exhibited characteristics which were identical with those at the outset.

(3) Test for effectiveness on filter paper

Measurements of fungistatic threshold were carried out to determine the activity of the microemulsion towards fungi responsible for the blue stain of timber by comparison with a conventional fungicide consisting of an aqueous solution of sodium pentachlorophenate (Na PCP).

The method of performing this test will now be described:

The principle consisted in exposing cellulose filter discs (37 mm diameter, 1 mm thickness), treated with the biocidal product under test, to infestation with the timber blue stain fungi employed as mixed cultures.

(3.1) Preparation of the discs

The discs were presoaked in an aqueous solution of malt extract (2%). After drying and being numbered, they were divided up into a number of series, in a proportion of 3 per fungus and per concentration investigated.

They were then subjected to the treatment which consisted of a 30-second immersion in the test emulsions and solutions, and were then left to dry for a week at ambient temperature (on the order to 20° C.), at the end of which they were sterilized using gamma irradiation.

(3.2) Experimental device

Each disc was placed, as indicated below, in a sterile Petri dish (90 mm diameter), prepared as follows: a presterilized glass ring 5 mm in height and with a diameter smaller than that of the discs was placed in the middle of the dish, and then a malt-agar medium (2%) was dispensed into the dish, under aseptic conditions, such as to cover the entire bottom of the dish around the glass ring, to a height not exceeding 3 mm.

After the culture medium had cooled and solidified, the glass ringrreceived a disc, deposited aseptically.

(3.3) Inoculation

The test fungi employed wee the following species:
(1) *Aureobasidium pullulans.*
(2) *Hormonema dematioides.*
(3) *Sclerophoma pityophila.*

The inoculation of the Petri dishes was performed by spraying both the culture medium and the disc uniformly using the spore suspension.

After inoculation, the Petri dishes were placed in an enclosure at 22° C.(+/−2° C.) and were subjected to continual supervision throughout the test period, fixed at 2 weeks.

(3.4) Examination at the end of the test

It should be noted that, by avoiding contact between the culture medium and the treated disc, the device employed eliminated any possibility of interaction between these two elements, capable of invalidating the experiment, particularly by possible diffusion of the product under test into the culture medium.

The examination at the end of the test concerned:

(i) the development of the fungi on the culture medium, demonstrating the validity of the test if it was carried out normally, that is to say, if the entire surface of this medium was invaded at the end of the test;

(ii) the degree of development of the fungi on each treated disc.

(3.5) Results

In the case of the microemulsion according to the invention, it was found that the effectiveness (or threshold of nondevelopment) ranged from 0.05% to 0.1%. This effectiveness is expressed in terms of concentration of fungicidal active substance in the microemulsion as ready for use.

In the case of the aqueous solution of Na PCP, it was found that the effectiveness ranged from 0.01% to 0.1%.

The biocidal product according to the present invention was, therefore, just as efficient as the Na PCP commonly employed for protecting timber (4) Test for effectiveness on timber This involved a test for the effectiveness of the emulsion in respect of the protection of fresh timber against the deep blue stain and the development of surface moulds.

A series of freshly sawn test specimens of Norway pine timber, 1 m (length)×15 cm (width)×27 mm (thickness) in size, were treated by soaking for 30 seconds in various fungicidal treatment products.

The fresh timber specimens were then inoculated by being subjected, by spraying, to the action of, on the one hand, a mixed culture of two fungi responsible for blue stain: *Aureobasidium pullulans* and *Hormonema dematioides* and, on the other hand, of a mixed culture of several fungi responsible for moulds: *Asperqillus niger, Asoerqillus flavus, Trichoderma viride, Penicillium spp* and *Cladosoorium spp.* These fungi were employed in the form of a spore suspension and it was this suspension which was sprayed over the timber.

Thus treated, the specimens were then placed outdoors on the earthen ground itself, in a number of groups of 9 specimens, the specimens belonging to the same group being stacked on each other in sets of three specimens and the said sets being separated from each other by boards of timber which had not been treated with a fungicidal product. Each group was placed inside a tunnel made of transparent plastic serving as a greenhouse, such as to promote the condensation which favors the development of moulds and to create optimum conditions for the development of the agents responsible for deep blue stain.

The incubation period varied, of course, as a function of the weather conditions at the time, but the results may be used as long as all the control boards which had not been treated with the fungicidal product were completely tainted on the surface due to the moulds. On average, this period required 7 weeks.

At the end of 7 weeks, therefore, the surface of each specimen was examined qualitatively (that is to say, on the one hand with the naked eye and, on the other hand, with a microscope), in order to detect the presence of fungal elements thereon. The intensity of the visible surface tainting (moulds) is expressed using the following scoring system:

0=no moulds,
=10% of the total surface of the specimen was tainted by moulds,
2=20% of the total surface of the specimen was tainted,
3=40% of the total surface of the specimen was tainted,
4=60% of the total surface of the specimen was tainted,
5=80% of the total surface of the specimen was tainted,
6=100% of the total surface of the specimen was tainted.

At the end of 10 to 12 weeks, the specimens were recovered for a destructive examination. Each specimen was sectioned in the transverse direction and the depth of timber, measured from the surface, which had acquired a blue stain was determined on each section using a magnifying glass and a microscope. The average depth, in mm, of timber which had become blue was shown for all the specimens.

The various fungicidal treatment products which had been tested in the manner indicated above were the following:

(i) the microemulsion prepared in paragraph (2) above;

(ii) an aqueous solution containing 1% by weight of Na PCP (test A);

(iii) an emulsion according to the prior art (BE-A-904,660) prepared from (test B):

(a) 1 part by weight of a concentrate having the following composition by weight (relative density at 20°=0.9564):

5.2% of azaconazole,
47.4% of benzalkonium chloride,
and 47.4% of propylene glycol monomethyl ether;
and (b) 20 parts by weight of water;

(iv) an emulsion which was not in accordance with the present invention, prepared from (test C):

(a) 1 part by weight of a concentrate having the following composition by weight (relative density at 20°C.=0.985):
5% 1% of azaconazole,
35.5% of benzalkonium chloride,
1.6% of a wide-spectrum, antimould fungicidal substance available commercially under the registered trademark Kathon 886 MW, which contained 13.9% by weight of a mixture of 2 fungicidal compounds: 5-chloro-2-methyl-4-isothiazolin-3-one and 2-methyl-4isothiazoline-3-one, 35,5% of propylene glycol monomethyl ether, and
22.3% water; and
(b) 29 parts by weith of water.

The results obtained are reported in the following table:

TABLE

| Treatment formulation | Surface moulds | Internal region which had become blue |
|---|---|---|
| That of the example according to the invention | 0 | 0 mm |
| That of test A | 1 | 2 mm |
| That of test B | 3 | 2 mm |
| That of test C | 2 | 0 mm |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A water-emulsifiable, liquid biocidal concentrate which comprises:

(A) a fungicidally effective amount of an active agent comprising:

(a1) at least one fungicidal compound having the formula:

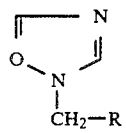

(I)

in which Q is N or CH; and R is one of the radicals:

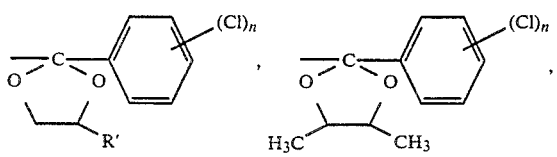

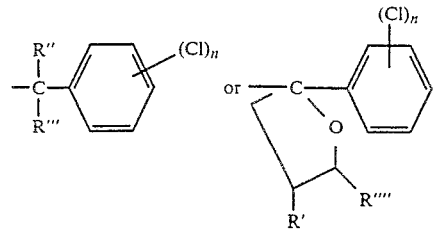

in which $R'$ is a hydrogen atom or a linear or branched chain alkyl radical containing from 1 to 3 carbon atoms, $R''$ is a hydrogen atom or a hydroxyl or cyano group, $R'''$ is a linear or branched chain alkyl radical containing from 1 to 6 carbon atoms, or a substituted such radical bearing a cycloalkyl or phenyl substituent, an alkenyloxy radical containing from 3 to 4 carbon atoms or a phenyl radical, or a substituted such radical bearing one or more halogen atom substituents, $R''''$ is a hydrogen atom or a linear or branched chain alkyl radical containing from 1 to 3 carbon atoms, or a substituted such radical bearing one or more halogen atom substituents, and n is an integer equal to 1 or 2;

(a2) at least one fungicidal compound having the formula:

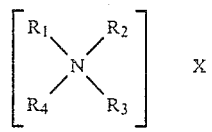

(II)

(cationic moiety)   (anionic moiety)

in which the cationic moiety of the salt has a total number of carbon atoms equal to or less than 50, and $R_1$, $R_2$, $R_3$ and $R_4$ are identical or different organic radicals, the free valency of which is borne by a carbon atom, with the proviso that one of the radicals $R_1$, $R_2$, $R_3$ or $R_4$ may be a hydrogen atom, or another ammonium group, and with the further provisos that two of such radicals may together form a single divalent radical, three of such radicals may together form a single trivalent radical, and two pairs of such radicals may together form two single divalent radicals; and the anionic moiety X is derived from an inorganic or organic acid; and (a3) at least one fungicidal compound selected from among:

(i) a benzimidazole compound having the formula:

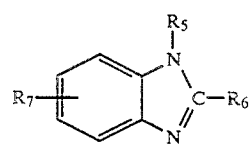

(III)

in which $R_5$ is a hydrogen atom or a —CO—NR$_8$R$_9$ group wherein $R_8$ is a hydrogen atom or a linear or branched chain alkyl radical containing from 1 to 4 carbon atoms and $R_9$ is a linear or branched chain alkyl radical containing from 1 to 6 carbon atoms, a phenyl radical or a benzyl radical, or a substituted such radical substituted by a lower alkyl group or a lower alkoxy group; R6 is a hydrogen atom, an amino group —$NH_2$, and —NH—CO—$OR_8$ group or an —NH—CO—NH—$OR_8$ group wherein $R_8$ is an alkyl radical as defined above, or a 4-thiazolyl group, with the proviso that $R_6$ may form a single ring with $R_5$ and the atoms to which these radicals are bonded; and $R_7$ is a hydrogen atom or a hydroxyl group; and (ii) a mixture of one or more of the benzimidazoles of formula (III) with one or more isothiazolinone compounds; and (B) a liquid carrier medium for said active agent (A) comprising (bl) at least two solvents (b1.1) and (b1.2), wherein (b1.1) comprises an ether of a lower alkanol containing from 1 to 4 carbon atoms and of a saturated aliphatic diol containing from 2 to 10 carbon atoms, and (b1.2) comprises a saturated aliphatic monocarboxylic acid containing from 1 to 6 carbon atoms.

2. The water-emulsifiable, liquid biocidal concentrate as defined by claim 1, said liquid carrier medium (B) further comprising at least one oil (b2) and/or at least one fixative (b3).

3. The water-emulsifiable, liquid biocidal concentrate as defined by claim 2, comprising, by weight:
(a) from 3% to 8% of the fungicidal compound(s) (a1);
(b) from 15% to 40% of the fungicidal compound(s) (a2);
(c) from 0.1% to 2% of the fungicidal compound(s) (a3);
(d) an amount of solvents (bl) equal to or greater than 50%; and
(e) from 0% to 20% of oil(s) (b2) and/or fixatives (b3).

4. The water-emulsifiable, liquid biocidal concentrate as defined by claim 1, wherein said at least one fungicidal compound (a1) having the formula (I), Q is N.

5. The water-emulsifiable, liquid biocidal concentrate as defined by claim 1, wherein said at least one fungicidal compound (a2) comprises a quaternary ammonium salt having the formula (II), in which $R_1$, $R_2$, $R_3$ and $R_4$ are saturated or unsaturated aliphatic, cycloaliphatic or aromatic hydrocarbon radicals; or radicals comprising recurring oxyalkylene units of the formula:

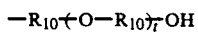

wherein t ranges from 1 to 10 and $R_{10}$ is one of the radicals —$CH_2$—, —$CH_2$—$CH_2$— or —$CH_2$—CH($CH_3$)—; with the proviso that one of the radicals $R_1$, $R_2$, $R_3$ or $R_4$ may be a quaternary ammonium radical of the formula:

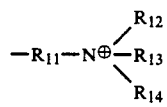

wherein $R_{12}$, $R_{13}$ and $R_{14}$ are hydrocarbon radicals or oxyalkylene radicals as defined above for $R_1$, $R_2$, $R_3$ and $R_4$, and $R_{11}$ is a divalent aliphatic or aromatic hydrocarbon radical in which the carbon chain(s) may be interrupted by oxygen atoms, and the free valencies of the radical $R_{11}$ being borne by aliphatic carbon atoms; and with the further proviso that one or more pairs of radicals $R_1$, $R_2$, $R_3$ and $R_4$ may together form single divalent alkylene or oxyalkylene radicals; and the anionic moiety X is from an organic or inorganic mono- or polyacid in which at least one of the acidic groups has a constant of ionization in water, $pk_a$, lower than or equal to 7.

6. The water-emulsifiable, liquid biocidal concentrate as defined by claim 1, said solvent medium (bl) comprising a ternary mixture (b1.1)+(b1.2)+(b1.3), wherein (b1.3) comprises a saturated aliphatic diol containing from 2 to 10 carbon atoms.

7. The water-emulsifiable, liquid biocidal concentrate as defined by claim 1, said solvent medium (bl) comprising the ternary mixture (b1.1)+(b1.2)+water.

8. The water-emulsifiable, liquid biocidal concentrate as defined by claim 1, said solvent medium (bl) comprising the quaternary mixture (b1.1)+(b1.2)+(b1.3)+water, wherein (b1.3) comprises a saturated aliphatic diol containing from 2 to 10 carbon atoms.

9. The water-emulsifiable, liquid biocidal concentrate as defined by claim 1, said solvent medium (bl) comprising from 60% to 95% by weight of solvent (b1.1) and 40% to 5% by weight of solvent (b1.2).

10. The water-emulsifiable, liquid biocidal concentrate as defined by claim 1, said active agent (A) further comprising (a4) at least one water-insoluble insecticidal compound.

11. The water-emulsifiable, liquid biocidal concentrate as defined by claim 10, said liquid carrier medium (B) further comprising a nonionic surface-active agent.

12. The water-emulsifiable, liquid biocidal concentrate as defined by claim 11, comprising, by weight
(a) from 3% to 8% of the fungicidal compound(s) (a1);
(b) from 15% to 40% of the fungicidal compound(s) (a2);
(c) from 0.1% to 2% of the fungicidal compound(s) (a3);
(d) from 1% to 10% of the insecticidal compound(s) (a4); than 20%;
(f) from 0% to 20% of oil(s) (b2) and/or of fixative(s) (b3); and
(g) from 5% to 20% of surface-active agent (b4).

13. A stable, low viscosity aqueous microemulsion comprising formulation, in water, of the liquid biocidal concentrate as defined by claim 1.

14. A water-emulsifiable, liquid biocidal concentrate according to claim 1, having an active agent (A) wherein (a1) is azaconazole, (a2) is a dimethylalkylbenzylammonium salt, (a3) is benomyl, and a liquid carrier (B) wherein (b1.1) is a propylene glycol monomethyl ether and (b1.2) is acetic acid.

15. In a method for the protection of sawn wood against deep blue stain and surface mould, the improvement which comprises utilizing as the preservative therefor, a biocidally effective amount of the microemulsion as defined by claim 13.

* * * * *